United States Patent [19]

Kock et al.

[11] 4,169,004
[45] Sep. 25, 1979

[54] WATER FRANGIBLE END SEAL FOR HYDRO-DISSOCIATIVE AGGLOMERATE TAMPON

[75] Inventors: Ronald W. Kock; Charles R. Hood; David L. Phillips, all of Cincinnati, Ohio

[73] Assignee: The Procter & Gamble Company, Cincinnati, Ohio

[21] Appl. No.: 822,296

[22] Filed: Aug. 5, 1977

Related U.S. Application Data

[62] Division of Ser. No. 616,213, Sep. 24, 1975, abandoned.

[51] Int. Cl.² ............................................. A61F 13/20
[52] U.S. Cl. .................................... 156/227; 156/272; 156/290; 156/553; 128/285
[58] Field of Search ............... 156/226, 227, 474, 221, 156/201, 204, 205, 290, 272, 553; 128/284, 285, 270

[56] References Cited

U.S. PATENT DOCUMENTS

| | | | |
|---|---|---|---|
| 2,589,777 | 3/1952 | Collins | 219/10.49 R |
| 2,799,759 | 7/1957 | Blond et al. | 219/10.53 |
| 2,908,601 | 10/1959 | Brown | 156/201 |
| 2,992,958 | 7/1961 | Yamaguchi | 156/273 |
| 3,232,810 | 2/1966 | Reeser | 156/273 |
| 3,575,767 | 4/1971 | Banks | 156/201 |
| 3,756,878 | 9/1973 | Willot | 128/284 |
| 3,812,856 | 5/1974 | Duncan et al. | 128/285 |
| 3,814,101 | 6/1974 | Kozak | 128/156 |
| 3,815,601 | 6/1974 | Schaefer | 128/285 |
| 3,849,227 | 11/1974 | Frieling et al. | 156/268 |
| 3,940,169 | 2/1976 | Kock | 289/1.5 |

OTHER PUBLICATIONS

"Techniques for Bonding Nonwovens," *Paper Film and Foil Converter*, Jan. 1973, at p. 30.

*Primary Examiner*—John T. Goolkasian
*Assistant Examiner*—William H. Thrower
*Attorney, Agent, or Firm*—E. Kelly Linman; John V. Gorman; Richard C. Witte

[57] ABSTRACT

In a tampon having an absorbent body which is an agglomerate of pieces of absorbent foam, said agglomerate being held together by an overwrap, the improvement wherein said overwrap is provided with a water frangible end seal formed exclusively of said overwrap material, said seal acting as a closure for said overwrap material before use and in vivo, but said seal opening up to permit dispersal of said agglomerate when the tampon is agitated in an excess of water such as a standard sewage disposal system.

8 Claims, 6 Drawing Figures

U.S. Patent  Sep. 25, 1979  Sheet 1 of 2  4,169,004
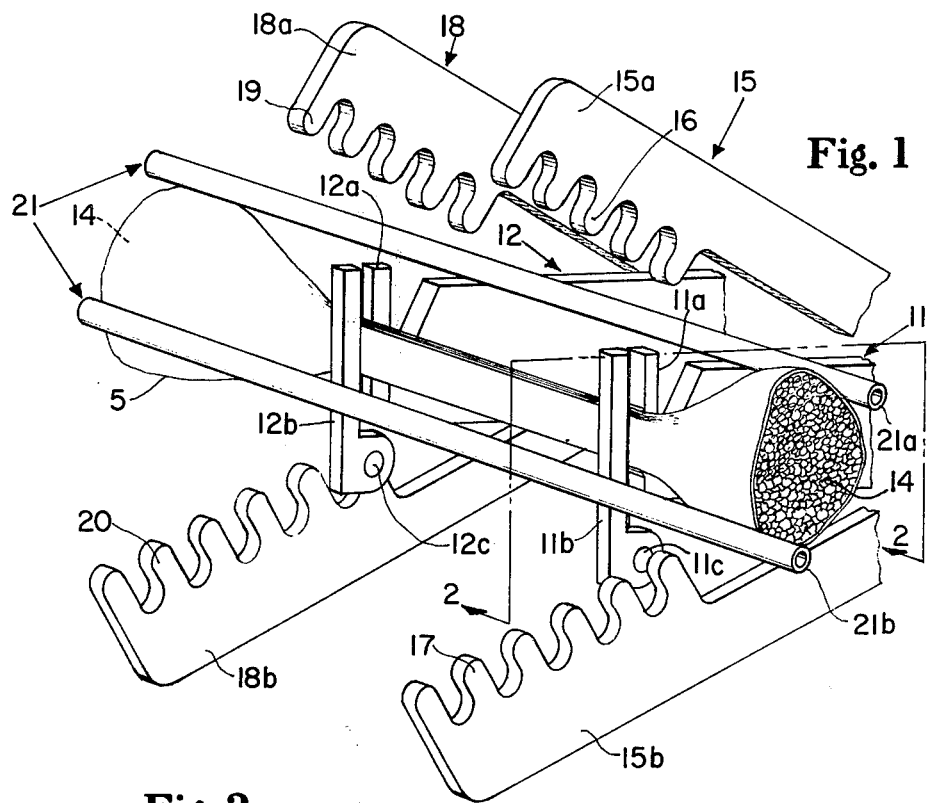
Fig. 1
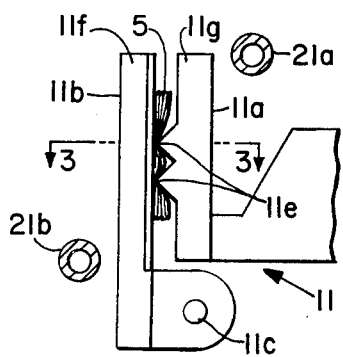
Fig. 2
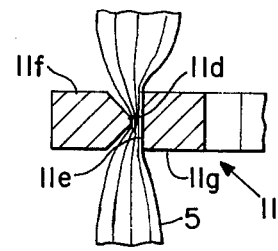
Fig. 3
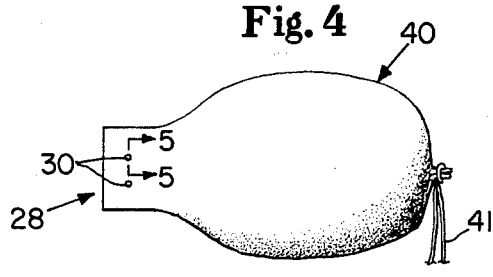
Fig. 4
Fig. 6

WATER FRANGIBLE END SEAL FOR HYDRO-DISSOCIATIVE AGGLOMERATE TAMPON

This is a division of application Ser. No. 616,213, filed Sept. 24, 1975 now abandoned.

FIELD OF THE INVENTION

This invention relates generally to absorbent structures designed to be disposed of in a standard sewage system. More particularly, it concerns disposable absorbent devices wherein the absorbent body is comprised of an agglomerate of distinct and separable pieces of foam, sponge, or other absorbent material encased by an overwrap.

DESCRIPTION OF THE PRIOR ART

Convenient disposal of single-use absorptive products has always presented a problem. Ordinarily, these absorptive products are disposed of with the ordinary solid garbage or in a water closet. The mode of disposal generally considered most convenient is flushing in a water closet. Some absorptive products, however, when not properly prepared, can clog water closet systems when excessive bulk is employed.

Many different absorptive materials are used in single use absorptive products, various fibers being the most commonly used. Although fibrous products present some water closet disposal problem, sponge, sponge-like and plastic foam products generally present greater water closet disposal problems due to the fact that they do not readily break down in a water closet system, and thus are more prone to clog water closet systems.

U.S. Pat. No. 3,812,856 which issued to Duncan et al. on May 28, 1974 and which is hereby incorporated herein by reference discloses a hydro-dissociative agglomerate tampon wherein at least one end of the gathered overwrap material employs a water frangible closure. In a particularly preferred embodiment, a water frangible adhesive is employed for this purpose.

Although water frangible adhesives function well to obtain the objectives stated in the Duncan et al. patent, any such adhesive must be not only physiologically safe for use in a tampon structure, but in addition, should preferably have an inverse temperature-water solubility property, i.e., it is insoluble at temperatures above a threshold temperature but is soluble at temperatures below that threshold. In particular, the adhesive should have a threshold temperature lower than normal body temperature to avoid premature opening of the end seal when the tampon is in use, yet higher than the sewage water temperature to permit effective opening when the structure is deposited in a water closet.

In addition to the added cost of the adhesive, means must be provided for applying the adhesive to the overwrap material at a predetermined location, means must be provided for effecting closure of the overwrap material at said predetermined location after the absorbent agglomerate has been inserted therein, and means must be provided for activating the adhesive to effect the seal. Preferred means for accomplishing the aforementioned steps are specifically disclosed in the copending, commonly-assigned application of Ronald W. Kock entitled Loop Knot Tying Method and Apparatus, Ser. No. 517,110, filed on Oct. 22, 1974, now U.S. Pat. No. 3,940,169 issued Feb. 24, 1976, said application and said patent being hereby incorporated herein by reference. The aforementioned application of Kock discloses preferred method and apparatus for producing agglomerate tampons of the type generally disclosed in U.S. Pat. No. 3,815,601 which issued to Schaefer on June 11, 1974, said patent also being hereby incorporated herein by reference. When agglomerate tampons are formed from a continuous tube of overwrap material, as disclosed in the aforementioned application of Kock, a peripheral glue stripe is preferably employed at uniformly-spaced locations along the length of the tube for effecting a water frangible end seal of the type disclosed in the aforementioned patent to Duncan et al. Thus, registration of the peripheral glue stripes with the clamping and sealing jaw assemblies utilized to activate the adhesive and form a water frangible end seal is a critical portion of the tampon manufacturing operation disclosed in the application of Kock.

OBJECTS OF THE INVENTION

Accordingly, it is an object of the present invention to provide a water frangible end seal comprised exclusively of the overwrap material in an agglomerate tampon of the type generally disclosed in the aforementioned patents to Duncan et al. and to Schaefer, said tampon being hydro-dissociative as taught by the patent to Duncan et al.

It is yet another object of the present invention to provide method and apparatus for effecting the aforementioned seal in the overwrap material.

SUMMARY OF THE INVENTION

In a preferred embodiment of the present invention a rivet-like seal interconnecting the opposite outermost surfaces of the gathered end portion of the heat sealable tampon overwrap material is formed by grasping the gathered overwrap material between a pair of sealing jaws having at least one pair of sharp edges aligned at approximately 90° to each other such that the gathered overwrap material is subjected to compression at the point or points of intersection between the jaws. The magnetic sealing jaws are preferably heated by passing them through an oscillating electromagnetic field provided by a high frequency power oscillator coupled to an induction heating coil. The result is that a tiny rivet-like seal is formed in the gathered overwrap material at the point of intersection of the crossed edges of the jaws. The rivet-like seal permits a multiplicity of layers of heat sealable overwrap material to be sealed together consistently and with high integrity, yet allows stress concentrations applied during product disposal by flushing in a water closet to break the seal and thus permit disgorging of the agglomerate absorbent material contained within the overwrap.

BRIEF DESCRIPTION OF THE DRAWINGS

While the specification concludes with claims particularly pointing out and distinctly claiming the subject matter which is regarded as forming the present invention, it is believed that the invention will be better understood from the following description taken in connection with the accompanying drawings, in which:

FIG. 1 is a simplified illustration of a continuous tube of tampon overwrap material held in a pleated configuration intermediate a pair of magnetic sealing jaws and a pair of non-magnetic clamping jaws as said jaws are passed intermediate the stationary segments of a high frequency induction heating coil;

FIG. 2 is a view taken along section line 2—2 of FIG. 1 showing the sealing jaws in the closed position as they pass between opposing segments of the induction heating coil;

FIG. 3 is an enlarged cross-sectional view taken along section line 3—3 of FIG. 2 illustrating the crossed-edge effect provided at the points of intersection between the sealing jaws and the overwrap material in a preferred embodiment of the present invention;

FIG. 4 is an illustration of an assembled tampon of the present invention after the water frangible end seal has been effected, the withdrawal string has been attached, and the structure has been severed from the continuous tube of overwrap material;

FIG. 6 is a cross-sectional view of a completed tampon assembly of the present invention after the reentrant portion of the overwrap material has been tucked into its final position prior to use.

DETAILED DESCRIPTION OF THE INVENTION

Figure 5:
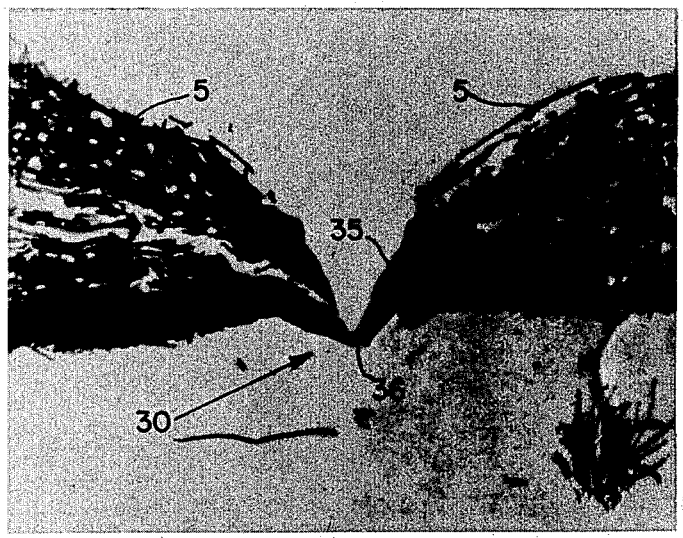
FIG. 5 is an enlarged cross-sectional photograph taken at a point corresponding to that of section line 5—5 of FIG. 4 illustrating a typical cross-section through a rivet-like seal formed in the overwrap material and extending from one outermost surface of the overwrap material to the opposite outermost surface thereof.

The present description has particular relation to method and apparatus for producing an agglomerate tampon as described in detail in the copending, commonly-assigned application of Ronald W. Kock entitled Loop Knot Tying Method and Apparatus, Ser. No. 517,110, said application having been incorporated herein by reference.

The product materials, in the particular exemplary application of the method and apparatus to be described herein, comprise a continuous tube of flexible, heat sealable material 5 having a substantially circular cross-section maintained by separate measured increments of aggregate material 14 located inside the tube and spaced one product pitch from each other. The apparatus of the present invention preferably comprises a drum (not shown) employing a multiplicity of stations, as described in the copending application of Kock. It is the function of each station contained on the periphery of the drum to form from the tube a discrete product comprising a bag-like structure having a water frangible seal at one end, closed with a withdrawal string at the other end, and containing one measured increment of aggregate material.

In a particularly preferred embodiment, the product material or tube 5 enters the stations of the drum tangentially from outside the drum. The feed means for the tube and the drum per se do not constitute a part of the present invention. Each station on the drum preferably performs the end sealing and loop knotting operations on one product or sack while said product or sack is a part of the continuous tube. After these operations have been completed, the sacks are cut from the tube to form individual products of the type generally shown in FIGS. 4 and 6. While preferred means for accomplishing the aforementioned objectives are disclosed in detail in the aforementioned copending application of Kock, applicants' invention resides in the provision of a novel, water frangible end seal in the tampon overwrap material. Accordingly, the present description shall be limited to this particular aspect of the tampon manufacturing operation broadly disclosed in the aforementioned application of Kock.

In FIG. 1 a clamping jaw assembly, a sealing jaw assembly, and a pair of pleating jaw assemblies are shown. The sealing jaw assembly is generally indicated at 11 and comprises a first sealing jaw 11a and a second sealing jaw 11b. The sealing jaw 11a is adapted to shift axially between open and closed positions. The second sealing jaw 11b is arranged to rotate between open and closed positions about pivot point 11c. In FIG. 1, the sealing jaws 11a and 11b are illustrated in their closed position. In the closed position, sealing jaws 11a and 11b contact and compress the pleated tube of overwrap material 5 at the points of intersection between the beveled edge 11d of jaw segment 11f and the teeth 11e of jaw segment 11g. A clamping jaw assembly, generally similar to the sealing jaw assembly 11, is generally indicated at 12 having a first clamping jaw 12a and a second clamping jaw 12b. The clamping jaws 12a and 12b are generally similar to sealing jaws 11a and 11b and are articulated in substantially the same manner. It should be noted, however, that only sealing jaws 11a and 11b are utilized to provide a water frangible end seal of the present invention in the tube of overwrap material 5. Accordingly, the edge of clamping jaw 12b is not beveled, and the clamping jaw 12a contains no teeth.

A first pleating jaw assembly is generally indicated at 15 and comprises an upper pleating jaw 15a and a lower pleating jaw 15b. Upper and lower pleating jaws 15a and 15b are illustrated in their open position in FIG. 1. In their closed position, the teeth 16 of upper pleating jaw 15a interdigitate with the teeth 17 of lower pleating jaw 15b with the tube of overwrap material 5 therebetween. A second pleating jaw assembly is generally indicated at 18 and comprises an upper pleating jaw 18a having teeth 19 and a lower pleating jaw 18b having teeth 20. The upper and lower pleating jaws 18a and 18b are substantially identical to upper and lower pleating jaws 15a and 15b and function in the same manner.

Once the pleating jaw assemblies 15 and 18 have formed pleats in the tube 5, the sealing jaw assembly 11 and the clamping jaw assembly 12, located between the pleating jaw assemblies, close upon the pleated tube. The jaws of both the sealing and clamping jaw assemblies move so that in their open position they will not interfere with the pleating step, yet in their closed position, they gather and secure the pleats as illustrated in FIGS. 1, 2 and 3.

Once the sealing and clamping jaw assemblies have secured the pleated tube, as illustrated in FIG. 1, the pleating jaw assemblies 15 and 18 are opened to avoid any interference with segments 21a and 21b of the induction heating coil 21 between which the sealing and clamping jaws travel. As shown in FIGS. 1 and 2, the stationary induction heating coil 21 is preferably mounted externally of the drum (not shown) on which the pleating jaws, sealing jaws, and clamping jaws are mounted. The induction heating coil 21 preferably comprises a long, narrow "U"-shaped structure curved to match the pitch circle of the drum. The coil may be of any suitable and well known construction. For example, in a working embodiment of the present invention, the coil is made up of quarter inch diameter copper tubing through which cooling water passes. On the outside of the coil a high frequency, alternating current is carried. As can be seen from FIG. 2, the sealing jaw assembly 11 is passed between the segments 21a and 21b of the "U"-shaped induction heating coil 21 in order to heat the sealing jaws and effect a water frangible seal of the present invention in the pleated tube of overwrap material 5.

Only the sealing jaw assembly 11 is intended to provide a sealing function. As a consequence, only those portions of the jaw abutting the pleated tube of overwrap material 5, i.e., portion 11f of jaw 11b and portion 11g of jaw 11a, are made of magnetic material such as carbon steel. The remaining support portions of the sealing jaws 11a and 11b, the entire clamping jaw assembly 12 and the other operating instrumentalities which pass between the segments 21a and 21b of the induction heating coil 21 are preferably made of non-magnetic materials such as austenitic stainless steel or the like so that the heating effect of the induction heating coil 21 is concentrated on those portions of the sealing jaw assembly 11 abutting the tube of pleated overwrap material 5, i.e., portions 11g and 11f of jaws 11a and 11b, respectively.

The high frequency oscillating electromagnetic field generated between the segments 21a and 21b of the induction heating coil 21 induces heat by magnetic hysterisis loss in the magnetic portions, i.e., portions 11g and 11f, of the clamping jaw assembly 11. In a preferred embodiment of applicants' invention, the sealing jaw segments 11g and 11f are provided with intersecting sharp edges such as shown in FIGS. 1, 2 and 3. This is accomplished by equipping the tube contacting surface of jaw segment 11f with a beveled edge 11d as shown in FIG. 3. Jaw segment 11g, on the other hand, is preferably equipped with one or more teeth 11e, as shown in FIG. 2. The intersecting land areas of the jaws actually making contact with the pleated tube 5 are preferably on the order of about 0.015 inches wide in order to reduce wear on the jaws at their points of intersection. As shown in FIGS. 2 and 3, the sharp edges of the sealing jaw segments 11f and 11g are oriented at 90° to each other at their points of contact with the pleated tube 5. Thus, pressure is applied to the pleated tube 5 by sealing jaw assembly 11 only at the points of intersection between the teeth 11e on jaw segment 11g and the beveled surface 11d of jaw segment 11f. Accordingly, both heat and pressure are concentrated on the overwrap material at the points of intersection of the jaws as the sealing jaw assembly 11 travels between the segments 21a and 21b of the induction heating coil 21. The concentration of heat and pressure at the points of intersection of the jaw segments 11f and 11g typically produces a pair of rivet-like seals formed exclusively of the heat sealable overwrap material 5, said rivet-like seals interconnecting the opposite outermost surfaces of the pleated overwrap material secured within the sealing jaw assembly 11 with one another. FIG. 5 is a photograph, enlarged approximately 25 times actual size, of one embodiment of a water frangible seal 30 of the present invention. The seal 30 is comprised of a rivet-like agglomerate 35 of overwrap material fused together by heat and pressure and extending from one outermost surface of the overwrap material to the opposite outermost surface thereof. A baffle 36 comprised of highly compressed overwrap material spans the interior surfaces of the rivet-like agglomerate 35. In yet another embodiment of the present invention which is generally similar to the embodiment shown in FIG. 5, a hole is formed completely through the layers of pleated overwrap material 5, thus eliminating the baffle 36, shown in FIG. 5.

Because a seal of the present invention is formed exclusively of the overwrap material 5, there is no need to precisely register a peripheral glue stripe as suggested in the copending application of Kock, thereby considerably simplifying the tampon manufacturing operation. Another significant advantage of the sealing technique disclosed herein resides in the fact that it minimizes the possibility of product contamination by adhesive since it completely eliminates the water frangible adhesive normally used to effect a water frangible end seal. Furthermore, a rivet-like or rivet-shaped seal of the type disclosed in FIG. 5 offers an additional advantage in that it is more reliably formed than a water frangible glue seal since there is less chance of the seal being adversely affected due to the presence of small amounts of absorbent material between the pleated layers of overwrap material 5 in the area of the seal. This is due to the fact that the profile of the sealing jaw segments 11f and 11g typically allows such seal contaminants to nest between the intersecting sharp edges of the jaws without holding the jaws apart. In addition, the concentration of heat and pressure at the intersecting sharp edges 11d and 11e of the jaw segments 11f and 11g can, in certain instances, seal completely through such contaminants.

Because of the small size and the localized nature of a rivet-shaped seal 30 of the type generally disclosed herein, fewer fibers of the heat sealable overwrap material are joined together. This is more clearly illustrated in the cross-section of FIG. 5. This not only enhances the wet openability of the structure, but has also been found to make the wet openability of the structure extremely reliable and consistent. In addition, there is no soak time requirement with such a seal, as in the case of a water frangible adhesive seal. Accordingly, the wet openability of a seal of the present invention is not time dependent. Unlike a water frangible adhesive seal which will dissolve if allowed to merely soak in water for a period of time, however, a water frangible rivet-like seal of the present invention is caused to open by the stress concentrations produced thereon. Accordingly, an agitated water bath such as a flushing toilet is generally preferred for rupturing a water frangible, rivet-like seal of the present invention.

In summary, a rivet-shaped seal 30 of the type generally described herein allows effective and consistent sealing of a multiplicity of layers of non-woven, heat sealable overwrap material with high integrity, yet allows stress concentrations applied to the seal during product disposal in a conventional water closet to break the seal and consequently enhance the disposability of the entire structure.

FIG. 6 is a fragmentary perspective view of a fully formed tampon 40 of the type illustrated in FIG. 4 after the sealed end 28 of the overwrap material 5 has been made reentrant, i.e., folded around one end of the agglomerate 14 and inwardly through a portion of the agglomerate. The sealed end 28 of the tampon shown in FIG. 6 has no proclivity toward opening before immersion in an agitated water bath due to the fact that the overwrap itself is flexible and does not tend to "spring back", and the forces exerted on the tampon before and during use are directed primarily radially inward. When, however, a tampon of this embodiment is introduced to an agitated water bath, the reentrant portion of the overwrap works outwardly, thereby providing a means of egress so that the pieces of absorptive material 14 are free to exert opening forces against the water frangible, rivet-shaped seals 30 in the pleated overwrap material 5. The opening and dissociative proclivities of any of the embodiments of the present invention which are produced by a swirling or agitated water bath are thought to exist because the pieces of absorptive material 14 move with the water currents and/or have inertial forces which create forces within the overwrap material 5 and which, after rupture of the water frangible seals 30, remove the absorptive material contained within the overwrap.

In a particularly preferred embodiment of the present invention, the overwrap 5 is comprised of a non-woven fabric, and the absorbent body 14 is comprised of an agglomerate of individual and separable pieces of a wet-swellable, polyurethane foam. This preferred embodiment can be inserted into a vagina by means of a telescoping, tube-type inserter, as is well known to those of ordinary skill in the tampon art. The tampon is resiliently compressed and is maintained in that condition before and during insertion by placing it in the outer tube of the inserter. The outer tube is inserted into the vagina and the tampon is ejected from the outer tube by pushing the inner tube so that it telescopes within the outer tube. The inserter is removed from the vagina after the tampon has been ejected from the outer tube.

The material used to form the tube of overwrap material 5 is perferably comprised of a smooth, soft, non-pilling, flexible, fluid-permeable, heat sealable, non-woven fabric. A biodegradable material for the overwrap is preferred. Several non-wovens which have functioned well as an overwrap are: Reemay, a hydrophobic, spunbonded, low basis weight, polyester non-woven fabric having a measured weight of about 0.4 ounces per square yard, available from E. I. DuPont de NeMours, Wilmington, Del.; Cerex, a 100 percent nylon non-woven fabric having a measured weight of about 0.4 ounces per square yard, available from Monsanto Company, St. Louis, Mo.; and Lutravil LS 5010 RX, a 100 percent polypropylene non-woven fabric having a measured weight of about 10 grams per square meter, available from Lutravil Spinnvlies GmbH & Company, Kaisersflautern, West Germany.

As will be apparent to those skilled in the induction sealing art, the temperature, time and pressure parameters employed to effect a seal or seals of the present invention will vary to some extent, depending upon such factors as the type of overwrap material employed, the softening temperature of the overwrap material, the number of layers of overwrap material to be sealed together, the desired degree of seal strength, the number of rivet-shaped seals to be effected, and the like. In a particularly preferred embodiment of the present invention, the sealing jaws 11a and 11b are spring-loaded in their closed position with a contact force amounting to between about 10 and about 15 pounds. Since the intersecting sharp edges 11d and 11e of the jaw segments 11f and 11g have a width of approximately 0.015 inches at their points of intersection, and the jaws intersect each other at two points, this corresponds to an applied pressure of between about 22,000 and about 33,000 pounds per square inch on the pleated overwrap material 5. Applicants have learned, for example, that pressures in the aforementioned range are generally effective to create a water frangible, rivet-shaped seal of the present invention on a pleated Reemay overwrap comprising a total of approximately 16 layers of material when the temperature of the jaw segments 11f and 11g is elevated to at least about 200° F., preferably to about 250° F. The temperature of the sealing jaw segments 11f and 11g rises continually as the jaw assembly 11 passes between the segments 21a and 21b of the induction heating coil 21 and decreases gradually after passing from the high frequency electromagnetic field existing between the coil segments. To soften the Reemay overwrap and produce a rivet-like seal 30 of the present invention it is necessary to maintain the jaw segments 11f and 11g at a temperature of at least about 200° F. for a period of at least about 0.5 seconds, preferably for a period between about 1.0 seconds and about 2.0 seconds. In a particularly preferred embodiment of the present invention, the induction heating coil 21 remains energized by the high frequency power oscillator (not shown) at all times, and the desired residence time of the sealing jaw assembly 11 between the coil segments 21a and 21b is achieved by adjusting the rotational speed of the drum (not shown) on which the sealing jaw assembly is mounted. In order to avoid overheating of the induction coil 21, cooling water is passed continuously through the interior of the coil. In normal operation the coil is de-energized only in the event the drum ceases rotation to avoid overheating of the sealing jaw segments 11f and 11g which stop therebetween, and thereby avoid oversealing or otherwise damaging the tube of overwrap material 5 retained within the sealing jaw assembly 11.

Although means other than induction heating could be employed to heat the jaw segments 11f and 11g and effect a rivet-shaped seal of the present invention, i.e., conduction heating, etc., it is believed that the present invention can be practiced to greatest advantage utilizing the induction heating technique generally described herein.

After the sealing jaw assembly 11 passes from between the induction heating coil segments 21a and 21b, the pleated overwrap 5 is maintained under compression for a period of time sufficient to permit cooling and solidifying of the rivet-shaped seals 30 formed therein. For an overwrap such as Reemay, this typically occurs by the time the magnetic jaw segments 11f and 11g have cooled to a temperature of approximately 150° F.

With the exceptions specifically noted and described herein, the remainder of the tampon manufacturing operations are generally in accordance with those illustrated and described in the aforementioned copending application of Kock, i.e., attachment of the withdrawal string 41 and severance of the individual tampons 40 from the continuous tube of overwrap material 5. The aforementioned operations are followed by tucking of the reentrant portion of the overwrap material at the sealed end 28 of the tampon 40 to form a finished tampon structure of the type generally illustrated in FIG. 6.

Thus, it is apparent that there has been provided, in accordance with the present invention, an absorptive device, as well as method and apparatus for producing same, that fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations which fall within the spirit and broad scope of the appended claims.

What is claimed is:

1. A method for providing a water frangible rivet-like seal in an end closure of a tubular, heat sealable, fluid-permeable overwrap material employed in an absorbent agglomerate tampon structure, comprising the steps of:

(a) gathering and pleating a terminal end of said tubular, fluid-permeable overwrap material to form a pleated end closure in said overwrap material;

(b) compressing said pleated end closure in said tubular, fluid-permeable overwrap material at a discrete, isolated location smaller in size than said pleated end closure;

(c) elevating the temperature of said pleated end closure in said fluid-permeable overwrap material at said discrete, isolated location by means of conduction while said overwrap is maintained under compression to at least the softening temperature thereof and maintaining said elevated temperature until said overwrap material is fused into a localized, rivet-like agglomerate comprised exclusively of said overwrap material and extending continuously from one outermost surface of said pleated end closure in said overwrap material to the opposite outermost surface thereof at said discrete, isolated location; and (d) cooling said overwrap material to a temperature below the softening temperature thereof while said overwrap material is maintained under compression at said discrete, isolated location to form a water frangible, rivet-like seal smaller in size than said pleated end closure and comprised exclusively of said overwrap material.

2. The method of claim 1, wherein said pleated end closure in said overwrap material comprises approximately 16 layers of heat sealable fabric having a measured weight of approximately 0.4 ounces per square yard and said pleated end closure of said overwrap material is compressed at said discrete, isolated location with a pressure of at least about 22,000 pounds per square inch.

3. The method of claim 2, wherein said overwrap material is elevated to a temperature of at least about 200° F. at said discrete, isolated location to fuse said overwrap material into a localized, rivet-like agglomerate extending continuously from one outermost surface of said pleated end closure in said overwrap material to the opposite outermost surface thereof at said discrete, isolated location.

4. An apparatus for producing a water frangible rivet-like seal in an end closure of a tubular, heat sealable, fluid-permeable overwrap employed in an absorbent agglomerate tampon structure, comprising:

(a) means for gathering and pleating a terminal end of said tubular, fluid-permeable overwrap material to form a pleated end closure in said overwrap material;

(b) means for compressing said pleated end closure in said tubular, fluid-permeable overwrap material at a discrete, isolated location smaller in size than said pleated end closure;

(c) means for elevating the temperature of said overwrap material at said discrete, isolated location by means of conduction while said overwrap is maintained under compression to at least the softening point thereof and thereafter maintaining said elevated temperature until said overwrap material is fused into a localized, rivet-like agglomerate comprised exclusively of said overwrap material and extending continuously from one outermost surface of said pleated end closure in said overwrap material to the opposite outermost surface thereof at said discrete, isolated location; and (d) means for cooling said overwrap material to a temperature below the softening point thereof while said overwrap is maintained under compression at said discrete, isolated location to form a water frangible, rivet-like seal smaller in size than said pleated end closure and comprised exclusively of said overwrap material.

5. The apparatus of claim 4, wherein said means for compressing said pleated end closure in said tubular overwrap is comprised of a pair of movable magnetic sealing jaws which in their closed position engage said pleated end closure therebetween only at said discrete, isolated location and said means for elevating the temperature of said overwrap material by means of conduction comprises said magnetic sealing jaws and a high frequency power oscillator coupled to an induction heating coil which heats said magnetic sealing jaws as they are passed therebetween.

6. The apparatus of claim 5, wherein said movable sealing jaws have intersecting sharp edges which in their closed position compress said pleated end closure in said overwrap material only at the points of intersection of said jaws.

7. The apparatus of claim 6, wherein the sharp edges of said sealing jaws have a width of approximately 0.015 inches at their points of intersection with one another.

8. The apparatus of claim 6, wherein said sealing jaws are resiliently loaded against one another in their closed position to exert a pressure of at least about 22,000 pounds per square inch on said pleated end closure in said overwrap material at the points of intersection of said jaws.

* * * * *